United States Patent [19]

Riedel

[11] 4,366,814
[45] Jan. 4, 1983

[54] ELASTIC BANDAGE MATERIAL

[75] Inventor: John E. Riedel, White Bear Lake, Minn.

[73] Assignee: Minnesota Mining and Manufacturing Company, St. Paul, Minn.

[21] Appl. No.: 251,336

[22] Filed: Apr. 6, 1981

[51] Int. Cl.³ .................................................. A61L 15/00
[52] U.S. Cl. ................................... 128/156; 128/169; 428/197; 428/230; 428/245; 428/343
[58] Field of Search ............... 128/81, 155–156, 128/160, 163–166.5, 169–170; 428/197, 230, 245, 260, 262, 265, 343

[56] References Cited

U.S. PATENT DOCUMENTS

| 3,127,306 | 3/1964 | Turton et al. | 428/197 |
| 3,483,018 | 12/1969 | Waldman | 117/68.5 |
| 3,542,634 | 11/1970 | Such et al. | 128/156 |
| 3,575,782 | 4/1971 | Hansen | 161/141 |
| 3,965,703 | 6/1976 | Barnhardt | 66/193 |
| 4,148,770 | 4/1979 | Stahle et al. | 428/265 |
| 4,173,131 | 11/1979 | Pendergrass et al. | 66/192 |
| 4,207,885 | 6/1980 | Hampton et al. | 128/156 |
| 4,236,550 | 12/1980 | Braun et al. | 128/156 |

FOREIGN PATENT DOCUMENTS

| 857077 | 11/1977 | Belgium . |
| 7802 | 2/1980 | European Pat. Off. |
| 54-40606 | 12/1979 | Japan . |
| 1449790 | 9/1976 | United Kingdom . |
| 1575830 | 10/1980 | United Kingdom . |

Primary Examiner—C. Fred Rosenbaum
Attorney, Agent, or Firm—Cruzan Alexander; Donald M. Sell; Carolyn A. Bates

[57] ABSTRACT

An elastic bandage material is disclosed comprising at least 50 percent by weight of an extensible fabric capable of elongation of at least 30 percent without tearing and at least 15 percent of an elastomer impregnated in a fabric but without filling the holes in the fabric. The bandage material is especially suited for use as a backing for adhesive tapes and dressings.

10 Claims, 1 Drawing Figure

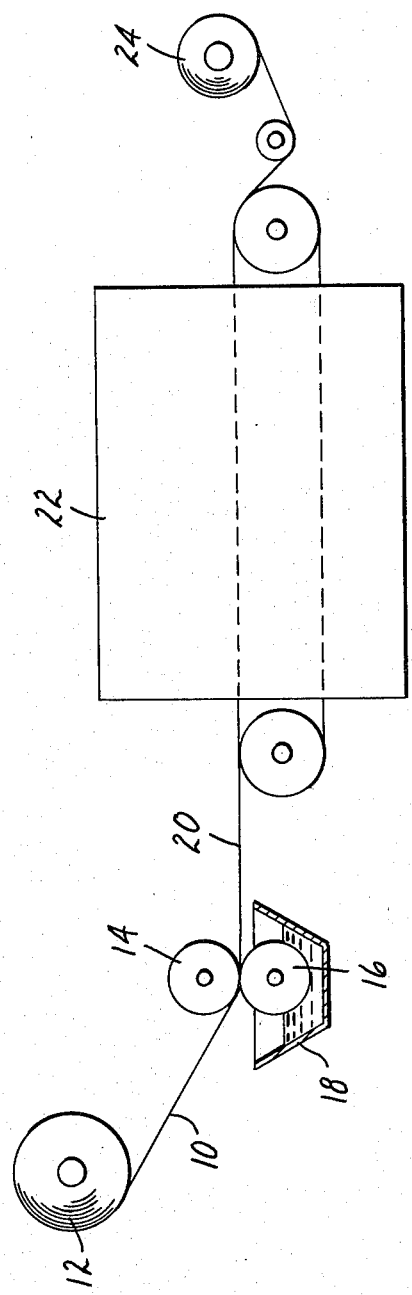

4,366,814

ELASTIC BANDAGE MATERIAL

FIELD OF THE INVENTION

This invention relates to elastic bandages for application to the body and elastic backings for medical and surgical tapes and dressings. A further aspect of the invention relates to medical and surgical tapes and dressings comprising the novel elastic backings of the invention.

BACKGROUND ART

Dressings and tapes applied to the skin should preferably exhibit a degree of stretchiness so that they do not unduly restrict movement of the underlying skin. This is particularly important in skin areas such as fingers, elbows and knees which are subjected to continuous stretching and relaxation during normal activities. If a tape does not exhibit elastic properties similar to or greater than skin, the tape will exert a force against the skin causing discomfort and in some cases, actual damage to the skin.

The prior art has devised numerous ways of providing elastic tapes and dressings. One popular method is to form loosely woven fabrics containing elastomeric filaments interspersed among non-elastomeric filler yarns. The elastomeric or rubbery filaments provide resiliency to the fabric, i.e., the ability to return to its original size and shape when the stretching force is removed. Typical constructions of this type are described in U.S. Pat. No. 4,207,885 and British Pat. No. 1,449,790. Stretchable knitted fabrics for use in elastic bandages are described in U.S. Pat. Nos. 3,965,703 and 4,173,131. An elastic bandage comprising elastic yarns sealed between two non-woven fibrous webs and between a non-woven fibrous web and a non-porous film are described in U.S. Pat. No. 3,575,782.

The aforementioned elastic fabrics are relatively expensive due, in part, to the elastomeric yarns, which are usually wrapped with non-elastomeric filaments. They are also generally bulky and often puckered in the relaxed state.

Less costly elastic non-woven fabrics of synthetic fibers bonded together at crossover points are described in Belgian Pat. No. 857,077 and Japanese Pat. No. 79040-606.

Dressings and tape backings having elastic properties have also been formed in layered or laminated constructions. European Pat. No. 7-802 describes a synthetic elastomeric fiber sheet made of bonded or non-bonded elastomeric fibers laminated to a less elastic sheet made of natural, synthetic or mineral fibers and/or filaments. British Pat. No. 1,575,830 describes an absorbent dressing such as a diaper comprising an elastomeric film backing laminated to an absorbent material which may comprise paper, wood pulp, or other absorbent material, preferably configured so as to be extensible such as by creping.

U.S. Pat. No. 3,483,018 describes an extensible adhesive tape in which the backing comprises an elastomeric film reinforced with an extensible fibrous substrate such as bias woven gauze having a maximum elongation of from about 20% to about 50%. The properties of the backing are primarily those of the elastomeric film which must be carefully selected to provide the required degree of moisture vapor transmission.

SUMMARY OF THE INVENTION

The present invention provides elastic bandage material for medical tapes and dressings possessing the strength and elasticity of the complex and costly woven fabrics containing elastic yarn, and the lightness and economy of the popular non-woven or light cloth materials. Tapes made from the bandage material possess the aesthetic appeal of fabric tapes, as contrasted with the sterile, plastic character of laminated or layered structures made from synthetic polymeric films.

The elastic bandage material of the present invention comprises: (1) at least 50 percent by weight of an extensible porous fabric capable of elongation of at least 30 percent in one direction without tearing; and (2) at least 15 percent by weight of an elastomer uniformly impregnated in the fabric and substantially contained on or within the fibers of the fabric without filling the spaces between fibers. A one-inch wide strip of the bandage material exerts at least a one-pound recovery force when elongated 20 percent.

The extensible porous fabrics useful in the practice of the invention are conventional fabrics which possess the requisite elongation properties thereby accommodating the stretching and twisting motion of the skin without providing opposing forces which cause discomfort and irritation. The fabrics alone, however, do not have sufficient elastic recovery to return quickly to their original shape when the original stretching and twisting force is removed. The elastic recovery properties of the bandage materials of the invention are conveniently and economically imparted by impregnating the fabric with a relatively small amount of an elastomer.

The useful degree of elastic recovery can be provided in these normally-inelastic fabrics without destroying their desirable ability to stretch under the application of very light force. A substantial amount of the elastomer is contained on or in the fibers of the fabric and does not form a continuous film or fill the spaces between the fibers. As a result, the fabric appears relatively unchanged and the elastomer has little or no effect on the oxygen and moisture vapor permeabilities of the original fabric.

DETAILED DESCRIPTION

Fabrics useful in the practice of the invention are generally loosely-woven or knitted to achieve the requisite elongation of at least 30 percent. Extensible non-woven fabrics may also be used. Fabrics capable of elongation of at least 100 percent without tearing are preferred. Many commercially-available fabrics such as knits, doubleknits and loose bias-cut wovens meet this criterion. Fabric construction may be of a wide range of synthetic or natural fibers, used singly or in blends. Presently preferred are knitted nylon and polyester fabrics.

The elastomers used to impart elastic recovery properties to the bandage materials of the invention are well known and generally include substances such as synthetic rubber or plastic, which, at room temperature, can be stretched under low stress to at least twice their original length, and, upon immediate release of stress, will return with force to their approximate original length (Dictionary of Scientific and Technical Terms, Daniel N. Lapedes, Editor-in-Chief, McGraw-Hill, 1974, p. 468). Preferred elastomers include block copolymers such as those of monovinyl aromatic hydrocarbons and conjugated dienes as described in U.S. Pat.

No. 3,265,765, polyurethanes, acrylics, acrylic-olefinic copolymers, and other natural and synthetic rubbers.

The preferred embodiment of the invention utilizes a doubleknit nylon fabric ("Antron" from Munsingwear, Minneapolis, Minn.) and a block copolymer of styrene and butadiene ("Kraton" 1101, Shell Chemical Co., Houston, Tex.).

The elastic bandage materials of the invention are easily made. The fabric is treated with a solution or dispersion of the elastomer, generally 10 to 30 percent solids, so that the fabric is completely saturated. Excess elastomer is then removed from the wet fabric, and the fabric is dried. After drying, the bandage materials should comprise at least 15 percent elastomer and preferably 20 to 35 percent elastomer.

DESCRIPTION OF THE DRAWING

The accompanying drawing illustrates the presently preferred method of manufacturing the elastic bandage material of invention, and is the method used to make the materials described in the examples hereinbelow.

The equipment used is of the type widely employed in the processing of non-woven webs. As is readily apparent to one skilled in the art, other equipment and procedures than those illustrated may be used without departing from the scope of the invention.

A continuous web of fabric 10 ("Antron" doubleknit) is led from a supply roll 12 to a set of nip rolls 14 and 16 with a pre-set gap. The lower nip roll 16 dips into a trough 18 containing a solution of elastomer ("Kraton" 1101, 20% in toluol) and transfers this solution to the passing web. The set-up is adjusted so as to transfer approximately 29% (by weight, after drying) "Kraton" 1101 to the web. For low-viscosity solutions of elastomer, the fabric may be dipped in the elastomer prior to passage through the nip rolls 14 and 16. After passing through the nip rolls 14 and 16, the wet web 20 is then passed through a drier 22, and the dried web is wound up on a roll 24. This web has the following properties:

Tensile at break: 70 pounds per inch width
Elongation at break: 275%
Tensile at 10% elongation: 1.0
Tensile at 20% elongation: 1.9
Tensile at 50% elongation: 4.8
Recovery, % and force after extension:

| —10% | 100%: | 0.9 lbs. |
| —20% | 100%: | 1.8 lbs. |
| —50% | 100%: | 4.4 lbs. |

The above data, as well as data presented in the examples below, were obtained using the following methods:
1. Tension of Elastic Materials: Federal Test Method Standard No. 191A.
2. Breaking Load and Elongation of Tensile Fabrics: ASTM Method No. D-1682-64.
3. Elastic Recovery. Elastic recovery was tested on an Instron tensile tester, Model No. TM-S. (Instron Corp., Canton, Mass.). Under standard conditions, 1-inch wide strips of test material were mounted in the jaws of the machine and stretched to the desired percent elongation. The sample was kept in this position until no more movement by the pen was observed on the chart recorder. The sample was then allowed to recover by decreasing the distance through which the strip had been stretched, and again observing the absence of movement on the chart recorder. A minimum of five different samples was used for each data point.

EXAMPLES

The following table shows examples of products made according to this invention. In each case the material was made in the same way as has been outlined above. In the table, examples without elastomer have been inserted as controls. The controls show the properties exhibited by the untreated fabrics. Comparison of the figures given for the controls with those of the same fabric with the elastomer gives an indication of the effect of the elastomer in increasing the ability of the fabric to recover from stretching. The absolute figures are not critical. One's choice will depend on the specific task the material is selected to perform. The low force figures (less than 1 pound) measured after extension of the control samples are typical of materials with insufficient elastic recovery to be useful, even though the ability to recover may be 100%. The higher force figures given for the materials of this invention (greater than 1 pound) indicate useful elastic recovery.

The woven cotton fabric of Examples 24–31 did not have the requisite elongation in the untreated state to be useful as a fabric in the bandage materials of the invention.

The materials used in the following examples are summarized as follows:

| Fabrics | Description | Supplier |
|---|---|---|
| "Antron" Doubleknit | Nylon doubleknit | Munsingwear 718 Glenwood Avenue Minneapolis, Minnesota |
| Burlington 4-113916 | Polyester knit | Burlington Knitted Fabrics 1345 Avenue of the Americas New York, New York 10019 |
| Guilford 15150 | Polyester knit | Guilford Mills, Inc. 222 West Adams St. Chicago, Illinois 60606 |
| Southern Silk 214 | Polyester knit | Southern Silk Mills P.O. Box 68 Spring City, Tennessee 37381 |
| Unbranded Doubleknit | Polyester/ cotton blend | |
| Woven Cotton | Cheesecloth | Pink Supply Co. 735 North Third St. Minneapolis, Minnesota 55401 |
| *Rayon Nonwoven | Staple fibers | Avtex Inc. 1185 Avenue of the Americas New York, New York 10036 |
| *Polyester Nonwoven | Staple fibers | Celanese Co. 1121 Avenue of the Americas New York, New York 11036 |
| "*Chisso" E. F. (Nonwoven) | Bicomponent fiber of polyester and polypropylene (crimped) | Chisso Corp. 6-32, Nakanoshima 3 Kita-Ku Osaka 530, Japan |
| "Lycra" Powernet | Dupont elastomeric in fabric | Fabric unbranded |

| Elastomers | Description | Supplier |
|---|---|---|
| "Kraton" 1101 | Block copolymer (styrene/ butadiene) | Shell Chemical Co. P.O. Box 2463 Houston, Texas 77001 |
| "Estane" 5702 | Polyurethane | B. F. Goodrich Co. 6100 Oak Tree Blvd. Cleveland, Ohio 44131 |
| Natural rubber | latex | E. P. Lampert Co. 1st National Tower 106 South Main St. Akron, Ohio |
| "Amsco" 4176 | SBR latex | Union Chemical Division Union Oil Company of Cal. |

| | | | | | | | | | Recovery % and lbs force after extension: | | | | | |
|---|---|---|---|---|---|---|---|---|---|---|---|---|---|---|
| | | | Percent Elastomer in final product | Tensile at Break | Elong$^n$ at Break | Tensiles at Elong$^n$ | | | 10% | | 20% | | 50% | |
| Ex. No. | Fabric | Elastomer | | | | 10% | 20% | 50% | % | lbs | % | lbs | % | lbs |
| | Nylon | | | | | | | | | | | | | |
| 1 | "Antron" Doubleknit 2.2 oz/sq.yd | none | 0 | 67 | 350 | 0.5 | 1.0 | 2.4 | 100 | 0.1 | 100 | 0.2 | 100 | 0.6 |
| 2 | "Antron" Doubleknit 2.2 oz/sq.yd | "Kraton" 1101 (20% in toluol) | 33 | 72 | 280 | 1.0 | 2.0 | 5.0 | 100 | 0.9 | 100 | 1.9 | 100 | 4.5 |
| 3 | "Antron" Doubleknit 1.8 oz/sq.yd | "Kraton" 1101 (20% in toluol) | 38 | 75 | 250 | 1.1 | 2.1 | 5.2 | 100 | 1.0 | 100 | 2.0 | 100 | 4.5 |
| 4 | "Antron" Doubleknit 1.8 oz/sq.yd | "Kraton" 1101 (20% in toluol) | 29 | 70 | 275 | 1.0 | 1.9 | 4.8 | 100 | 0.9 | 100 | 1.8 | 100 | 4.4 |
| 5 | "Antron" Doubleknit 1.8 oz/sq.yd | "Kraton" 1101 (15% in toluol) | 20 | 70 | 280 | 0.9 | 1.9 | 4.5 | 100 | 0.8 | 100 | 1.7 | 95 | 3.5 |
| 6 | "Antron" Doubleknit 1.8 oz/sq.yd | "Kraton" 1101 (10% in toluol) | 14 | 67 | 300 | 0.7 | 1.4 | 2.8 | 100 | 0.6 | 100 | 1.0 | 90 | 1.8 |
| 7 | "Antron" Doubleknit 1.8 oz/sq.yd | "Kraton" 1101 (5% in toluol) | 7 | 67 | 330 | 0.6 | 1.2 | 2.5 | 100 | 0.3 | 100 | 0.6 | 90 | 1.3 |
| | Polyester | | | | | | | | | | | | | |
| 8 | Burlington 4-113916 | none | 0 | 18.3 | 163 | 0.1 | 0.2 | 0.7 | 100 | 0.05 | 100 | 0.1 | 90 | 0.2 |
| 9 | Burlington 4-113916 | "Kraton" 1101 (20% toluol) | 35 | 29.0 | 112 | 2.5 | 4.3 | 10.1 | 100 | 2.3 | 100 | 3.9 | 90 | 8.6 |
| 10 | Burlington 4-113916 | "Estane" 5702 (20% M.E.K.) | 33 | 34.5 | 107 | 2.7 | 5.2 | 14.2 | 100 | 2.0 | 95 | 3.9 | 85 | 8.5 |
| 11 | Burlington 4-113916 | Natural Rubber Latex 20% | 38 | 29.0 | 127 | 0.8 | 1.7 | 5.5 | 100 | 0.7 | 100 | 1.4 | 84 | 4.1 |
| 12 | Burlington 4-113916 | "Amsco" 4176 | 32 | 26.5 | 105 | 1.0 | 2.0 | 7.2 | 100 | 0.8 | 100 | 1.5 | 88 | 4.2 |
| 13 | Burlington 4-113916 | "Rhoplex" 2970 (Acrylic-Styrene latex, 20%) | 36 | 26.5 | 107 | 0.7 | 1.4 | 5.2 | 100 | 0.5 | 95 | 0.6 | 70 | 0.3 |
| 14 | Burlington 4-113916 | "Rhoplex" 1715 (Acrylic latex 20%) | 35 | 22.2 | 112 | 3.0 | 5.3 | 10.8 | 100 | 1.8 | 95 | 1.3 | 75 | 1.1 |
| 15 | Burlington 4-113916 | "Kraton" 1101 (20% toluol) | 21 | 20.1 | 132 | 1.7 | 3.1 | 7.9 | 100 | 1.5 | 100 | 2.6 | 90 | 6.7 |
| 16 | Guilford 15150 | none | 0 | 10.1 | 4.3 | 0.8 | 2.3 | — | 100 | 0.3 | 100 | 0.9 | — | — |
| 17 | Guilford 15150 | "Kraton" 1101 (20% toluol) | 24 | 9.8 | 4.0 | 1.8 | 3.9 | — | 100 | 1.6 | 98 | 3.6 | — | — |
| 18 | Southern Silk 214 | none | 0 | 52.8 | 78 | 1.3 | 8.0 | 32.9 | 100 | 0.5 | 95 | 3.2 | 80 | 12.5 |
| 19 | Southern Silk 214 | "Kraton" 1101 (20% toluol) | 22 | 43.1 | 70 | 7.5 | 15.7 | 31.1 | 95 | 14.1 | 85 | 28 | | |
| 20 | Unbranded Doubleknit 3.6 oz/sq.yd. | none | 0 | 50 | 220 | 0.9 | 2.1 | 7.9 | 100 | 0.2 | 100 | 0.4 | 100 | 0.4 |
| 21 | Unbranded Doubleknit 3.6 oz/sq.yd. | "Kraton" 1101 (20% toluol) | 31 | 58 | 135 | 2.0 | 5.0 | 9.8 | 100 | 1.8 | 100 | 4.5 | 100 | 9.0 |
| 22 | Unbranded Doubleknit (4.0 oz/sq.yd) | none | 0 | 35 | 120 | 0.6 | 1.7 | 5.0 | 100 | 0.2 | 100 | 0.5 | 100 | 1.0 |
| 23 | Unbranded Doubleknit (4.0 oz/sq.yd) | "Kraton" 1101 (20% toluol) | 30 | 30 | 100 | 2.0 | 4.0 | 8.3 | 100 | 1.9 | 100 | 3.6 | 100 | 7.3 |
| | Cotton | | | | | | | | | | | | | |
| 24 | (unbranded) 40 × 32 | none | 0 | 15.0 | 6 | — | — | — | — | — | — | — | — | — |
| 25 | (unbranded) 40 × 32 | "Kraton" 1101 (20% toluol) | 26 | 13.6 | 10 | 13.6 | — | — | 95 | 9.5 | — | — | — | — |
| 26 | (unbranded) 40 × 32 | "Estane" 5702 (20% M.E.K) | 30 | 13.6 | 10 | 13.6 | — | — | 100 | 11.5 | — | — | — | — |
| 27 | (unbranded) | Natural Rubber | 33 | 18.3 | 13 | 14.9 | — | — | 100 | 13.7 | — | — | — | — |

*Made from staple fibers purchased from the manufacturer indicated.

-continued

PROPERTIES OF THE NEW MATERIALS

| Ex. No. | Fabric | Elastomer | Percent Elastomer in final product | Tensile at Break | Elong$^n$ at Break | Tensiles at Elong$^n$ 10% | 20% | 50% | Recovery % and lbs force after extension: 10% % | lbs | 20% % | lbs | 50% % | lbs |
|---|---|---|---|---|---|---|---|---|---|---|---|---|---|---|
| 28 | 40 × 32 (unbranded) | Latex 20% "Amsco" 4176 (SBR Latex 20%) | 35 | 18.7 | 15 | 10.5 | — | — | 100 | 5.6 | — | — | — | — |
| 29 | 40 × 32 (unbranded) | "Rhoplex" 2970 (Acrylic-Styrene Latex 20%) | 32 | 17.3 | 10 | 17.3 | — | — | 100 | 2.6 | — | — | — | — |
| 30 | 40 × 32 (unbranded) | "Rhoplex" 1715 (Acrylic Latex 20%) | 32 | 17.1 | 10 | 17.1 | — | — | 100 | 2.6 | — | — | — | — |
| 31 | (unbranded) (Bias cut) | none | 0 | 8.7 | 33 | 0.1 | 0.3 | — | 100 | 0.05 | 100 | 0.1 | — | — |
| 32 | (unbranded) (Bias cut) | "Kraton" 1101 (20% toluol) | 29 | 31.0 | 20 | 17.5 | 31.0 | — | 95 | 14.0 | 95 | 27.9 | — | — |
| 33 | (unbranded) (Bias cut) | Natural Rubber Latex 20% | 33 | 17.0 | 23 | 3.0 | 13.0 | — | 95 | 2.0 | 80 | 7.8 | — | — |
| Nonwovens | | | | | | | | | | | | | | |
| 34 | Rayon 1.5 denier, 1.5" | "Rhoplex" 2970 20% | 31 | 6.9 | 24.3 | 3.7 | 6.3 | — | 50 | 0.2 | 55 | 0.6 | — | — |
| 35 | Polyester 1.8 denier, 1.5" | "Rhoplex" 2970 20% | 33 | 5.7 | 26.5 | 2.4 | 5.1 | — | 4 | 0.2 | 50 | 0.4 | — | — |
| 36 | "Chisso" E.S. (3.0 denier, 1.5") | "Rhoplex" 2970 20% | 30 | 6.2 | 15.6 | 3.0 | — | — | 55 | 0.3 | — | — | — | — |
| 37 | "Chisso" E.S. (3.0 denier, 1.5") | "Kraton" 1101 (20% toluol) | 33 | 9.1 | 20.9 | 5.7 | 9.0 | — | 100 | 5.2 | 80 | 7.8 | — | — |
| Knitted Rubber Fabric | | | | | | | | | | | | | | |
| 38 | "Lycra" Powernet 1.8 oz/sq.yd | none | 0 | 33 | 625 | 0.4 | 0.7 | 1.0 | 100 | 0.4 | 100 | 0.7 | 100 | 1.0 |
| 39 | "Lycra" Powernet 1.8 oz/sq.yd | "Kraton" 1101 20% toluol | 24 | 36 | 575 | 0.6 | 0.9 | 1.9 | 100 | 0.6 | 100 | 0.9 | 100 | 1.9 |

The bandage materials of the invention are preferably used as stretch bandages and backings for adhesive tapes and dressings. Tapes and dressings may be coated in the conventional manner (See U.S. Pat. No. 3,121,021) with a pressure-sensitive adhesive such as that described in U.S. Pat. No. Re 24,906. First aid dressings comprising the elastic bandage material of the invention coated with a layer of pressure sensitive material and having a medicated or non-medicated wound-contacting area to prevent the adhesive from sticking to the wound are also a preferred embodiment of the invention. Typical constructions are described in U.S. Pat. Nos. 2,946,435; 4,182,449 and 4,192,299.

What is claimed is:

1. An elastic bandage material comprising:
   (a) At least 50 percent by weight of an extensible fabric made up of fibers and capable of elongation of at least 30 percent without tearing, and
   (b) at least 15 percent by weight of an elastomer uniformly impregnated in said fabric and contained substantially on or within said fibers without filling the spaces between said fibers; a one-inch strip of said bandage material being capable of exerting at least a one-pound recovery force when elongated 20 percent.

2. The bandage material according to claim 1 wherein said fabric is selected from the group consisting of knits, wovens and nonwovens comprising natural or synthetic fibers or blends thereof.

3. The bandage material according to claim 2 wherein said fabric is doubleknit nylon.

4. The bandage material according to claim 1 wherein said elastomer is selected from the group consisting of block copolymers of monovinyl hydrocarbons and conjugated dienes, polyurethanes, and acrylics and acrylic olefinic copolymers.

5. The bandage material according to claim 4 wherein said elastomer is a block copolymer of monovinyl hydrocarbons and conjugated dienes.

6. The bandage material according to claim 5 wherein said elastomer is a copolymer of styrene and butadiene.

7. The bandage material according to claim 1 wherein said fabric is capable of elongation of at least 100 percent without tearing.

8. The bandage material according to claim 1 comprising between 20 and 35 percent by weight of said elastomer.

9. The bandage material according to claim 1 further comprising a layer of pressure-sensitive adhesive.

10. The bandage material according to claim 9 further comprising a non-tacky wound-covering area.

* * * * *

UNITED STATES PATENT AND TRADEMARK OFFICE
CERTIFICATE OF CORRECTION

PATENT NO. : 4,366,814
DATED : January 4, 1983
INVENTOR(S) : JOHN E. RIEDEL

It is certified that error appears in the above—identified patent and that said Letters Patent is hereby corrected as shown below:

Column 6, Example 19, Recovery % and lbs force after extension should be:

| 10% | | 20% | | 50% | |
|---|---|---|---|---|---|
| % | lbs | % | lbs | % | lbs |
| 95 | 6.8 | 95 | 14.1 | 85 | 28 |

Signed and Sealed this

Ninth Day of August 1983

[SEAL]

Attest:

GERALD J. MOSSINGHOFF

Attesting Officer    Commissioner of Patents and Trademarks